(12) United States Patent
Gutierrez Gonzalez

(10) Patent No.: US 12,102,584 B2
(45) Date of Patent: Oct. 1, 2024

(54) MOTORIZED ASSISTANCE SYSTEM

(71) Applicant: Noel Gutierrez Gonzalez, Asturias (ES)

(72) Inventor: Noel Gutierrez Gonzalez, Asturias (ES)

( * ) Notice: Subject to any disclaimer, the term of this patent is extended or adjusted under 35 U.S.C. 154(b) by 1135 days.

(21) Appl. No.: 16/765,818

(22) PCT Filed: Nov. 20, 2018

(86) PCT No.: PCT/ES2018/070747
§ 371 (c)(1),
(2) Date: Nov. 9, 2020

(87) PCT Pub. No.: WO2019/102052
PCT Pub. Date: May 31, 2019

(65) Prior Publication Data
US 2021/0052458 A1    Feb. 25, 2021

(30) Foreign Application Priority Data

Nov. 23, 2017  (ES) ................. P201731352

(51) Int. Cl.
*A61H 3/00* (2006.01)
*A61F 5/01* (2006.01)
(Continued)

(52) U.S. Cl.
CPC ............ *A61H 3/00* (2013.01); *A61F 5/0123* (2013.01); *A61F 5/0127* (2013.01); *A61H 1/024* (2013.01);
(Continued)

(58) Field of Classification Search
CPC ........ A61H 3/00; A61H 1/0266; A61H 1/024; A61F 5/0111; A61F 5/0113; A61F 5/0123; A61F 5/0127; B25J 9/00; B25J 9/104
See application file for complete search history.

(56) References Cited

U.S. PATENT DOCUMENTS 5,112,296 A    5/1992  Beard et al.
2009/0299243 A1   12/2009  Hirata et al.
(Continued)

FOREIGN PATENT DOCUMENTS

KR    101703634 B1    2/2017

OTHER PUBLICATIONS

International Search Report for corresponding PCT/ES2018/070747.
(Continued)

*Primary Examiner* — Brian A Dukert
(74) *Attorney, Agent, or Firm* — Egbert, McDaniel & Swartz, PLLC

(57) ABSTRACT

Disclosed is a motorized assistance system with a tibial orthosis including: a tibial fastening that covers the user's shin; an ankle fastening articulated with a plantar fastening at the axis of the ankle; and a processor. The tibial fastening can include a support of a motorized winch, in which a strap is hooked, whose free end is fixed to the foot, so that the winch takes up the strap when a foot position sensor indicates that it is not resting on the ground. Alternatively, the system can have a femur orthosis with two femur actuators that take up or release two strap in parallel, one attached to a harness or belt and the other to the tibial fastening. The system may include additionally or alternatively a hip orthosis.

15 Claims, 3 Drawing Sheets

(51) Int. Cl.
*A61H 1/02* (2006.01)
*A41D 13/05* (2006.01)

(52) U.S. Cl.
CPC ....... *A61H 1/0266* (2013.01); *A41D 13/0543* (2013.01); *A61H 2003/007* (2013.01); *A61H 2201/149* (2013.01); *A61H 2201/1642* (2013.01); *A61H 2201/1652* (2013.01); *A61H 2201/5007* (2013.01); *A61H 2201/5064* (2013.01); *A61H 2201/5071* (2013.01); *A61H 2201/5084* (2013.01)

(56) References Cited

U.S. PATENT DOCUMENTS

| | | | |
|---|---|---|---|
| 2013/0046218 A1* | 2/2013 | Wiggin | A61F 5/0127 602/16 |
| 2016/0250094 A1* | 9/2016 | Amundson | A61H 1/024 623/24 |
| 2017/0027802 A1 | 2/2017 | Jang et al. | |

OTHER PUBLICATIONS

Written Opinion of the ISA for corresponding PCT/ES2018/070747.
Written Opinion of the IPEA for corresponding PCT/ES2018/070747.
International Preliminary Report on Patentability for corresponding PCT/ES2018/070747.

* cited by examiner

MOTORIZED ASSISTANCE SYSTEM

TECHNICAL FIELD

The present invention relates to a motorized assistance system, exoskeleton, which in its most complete version corresponds to a set of three orthoses that reproduce the movements of the leg's muscles allowing that an individual with a locomotive disability, but with normal lower limbs, could walk. In the simplest version it corresponds to a corrective tibial orthosis of the drop foot, allowing normal movement to those affected by this dysfunction. It is applicable in the field of orthopaedics and rehabilitation.

STATE OF THE ART

Motorized displacement assistance systems, popularly known as exoskeletons, are based on lateralized systems, an articulated metal frame runs along the sides of the limbs and a series of motors that help or fully provide the locomotive function are inserted in them.

Its basic mechanism of action is to lift the patient's body by means of motors, which must withstand a large workload (almost the total weight of the patient plus their own).

The weight of said exoskeletons, although investigated and constantly tried to reduce, is considerable. In addition, since the weight is distributed on the side (motors and exoskeleton itself), the centre of gravity of the patient changes completely when moving, being necessary the use of gyroscopes and inertia sensors, which constantly correct the motor to keep the simple balance of the patient/exoskeleton system itself when walking.

This combination of motor power, sensors, weight, and distribution that in no way reproduce the biomechanics of the human being, make the final product considerably more expensive.

On the other hand, and as a sign of the degree of modularity of the system, we will focus on one of simpler combinations, as a functional solution to a specific motor disorder. The so called "drop foot", is a dysfunction that prevents upward movement of the toe, and therefore makes walking difficult and makes it impossible to run. In order to be able to walk, the patient develops, in various ways, an overcompensation to alleviate his deficiency, resulting in a limp that leads to another series of problems when overloading muscle groups and causing the joints to have a movement, a forced turn or both. Its causes are varied, but the treatment is usually by orthosis.

When neither the muscle nor the tibial nerve have been affected (there is no trauma, or demyelination process), devices have been developed that stimulate said nerve, replacing the impulse arising from the central nervous system, by a small discharge in said nerve, just by under the knee, which activates normal muscle functioning. If there is a nervous, degenerative, traumatic or muscular condition, these devices are useless.

The developed orthoses are included under the name AFO (Ankle Foot Orthosis), and are very varied. From those that only perform a passive stabilization of the foot, keeping it constantly at 90 degrees, to the dynamic ones, which basically perform a pushing action on the base of the foot, by means of the mechanism of leveraging on the calf muscles. The most advanced of the latest, even allow running. These systems are purely mechanical.

There are also purely electronic prototypes, which have not been commercialized due to the problems they comprise, such as the need for a large battery or electronic equipment.

The main form of the invention would be included in this second type of orthosis, as it comprises electronic equipment that coordinates the active elements of the orthosis, but with a very small cost and number of elements.

As for hip prostheses, US2017027802 is known, as well as the oldest US 2009/0299243, which has a belt with two motors and two stems, one on each side of the user. This system is effective when you want to act on both legs, to create a pendulum movement, and simply act as an aid in locomotion. On the other hand, it cannot serve as a substitute for complete muscle movement. If these orthoses are applied to assist in the movement of a single leg, the user is decompensated, generating risks of falls or injuries. If it were desired to perform a single leg movement with said devices, an entire lower exoskeleton would be needed, at least in said limb to be able to compensate for unwanted movements, and an exponential increase in energy requirements. No solution even mentions such possible use on one leg.

Another relevant disclosure is the device of US2016/0250094A1 that might be considered the closest prior art. It pertains to a motorized tibial orthosis with a tibial and a plantar fastening. It also comprises sensors for knowing the position of the foot.

BRIEF EXPLANATION OF THE INVENTION

The invention consists of a motorized assistance system according to the claims.

The motorized assistance system is a paradigm shift in these systems, one may say that it is an "exomuscular" system, rather than a regular exoskeleton. It reproduces the behaviour of the muscles and tendons themselves, on the same axis, sense and direction, causing the joint, with minimal energy, to behave as it normally would. That is, it faithfully reproduces the biomechanics of the locomotor system.

It is based on the swinging movement that the human being naturally performs when walking, unloading the leg that we are going to move, so it is not necessary so much power in the motors, as in the current exoskeletal systems, drastically reducing also the energy consumption.

It gets a perfect biomechanics, equal to that performed naturally by people without injury or disability.

In the case of the drop foot, it allows to run naturally. It does not require a constant effort on the calf muscle as some mechanical orthoses perform. On the other hand, it requires a small effort on the part of the user, so it does not atrophy the muscles.

In the complete system we load the weight on the leg that is fixed, while we unload the weight of the one we are going to move, using the minimum energy in each movement.

Conventional exoskeletons lift the entire body weight, regardless of or without taking advantage of (as far as one can see), such a swinging.

The current prototype has been designed thinking of people with reduced mobility, walking on crutches, for example, or having different types of disabilities, but not for total paraplegics (without any control over the lower limbs)

The system consists of three sections that, together and under command of a processor, or central microcontroller (CPU), which sets the times and angles of rotation of the servomotors, actuators or different active parts, act on the orthoses, reproducing the inherent movements of the muscles when walking, getting the gradual, preprogramed mobilization of the limb.

The system consists of three orthoses (tibia, femur/thigh and hip) that can be assembled more or less independently according to the patient's own needs, or together, so that all inherent movements of the leg are performed autonomously when walking.

In particular it has a tibial orthosis, especially applicable to correct the drop foot, with a tibial fastening that covers the user's shin, for example, a shin guard. An ankle fastening, articulated at the axis of the ankle with a plantar fastening. It also comprises a processor or controller of the orthosis and its power supply.

In addition, the tibial fastening comprises a support of one or, preferably, two motorized winches, with straps. The free end of the first strap, or front strap, is fixed to the front of the foot. In the simplest solution ("drop foot"), the winch takes up the front strap when a foot position sensor indicates that it is not resting on the ground.

In the most complete solution, in addition to this first described movement, the second winch does the same to a strap hooked to the back of the shoe ("back strap"), raising the heel to a signal either from one sensor or another activator. Both movements are opposite and alternative, (heel lift, toe lift).

As examples of foot position sensors are mentioned one or more pressure sensors arranged in the plantar fastening and one or more accelerometers or gyroscopes.

In the simplest solution, the processor and the power supply are equally carried in the support.

For its part, the free end of the front strap can be fixed to the foot by many methods, the most practical being:
- A loop capable of surrounding the foot. For example, a flange that will be discarded because it is dirty.
- A hook in the shoe, which must be designed on purpose to resist these tensions.
- A hook in an extension of the plantar fastening.

The free end of the back strap would ideally be hooked directly to the footwear, modified for this purpose on the back sides after the ankle, near the heel, so that the footwear is raised directly and also the heel itself.

Strap bypass pulleys can be installed on the support to facilitate the orientation thereof.

For the control of the winch load, several standards can be defined. The first one is to ensure that the winch releases (and retakes) an adjustable amount of strap. The second one is to stop the winch when the strap resistance exceeds a programmable limit. To this end a load sensor on the winch or its motor will be included.

The invention may also comprise a femur orthosis, located above the knee. It consists of a small system on the thigh that serves as the basis for two femur actuators:
- The lower femur actuator is attached by a strap, preferably adjustable, to the tibial orthosis, producing knee extension when operated. The folding of the knee (partial flexion) is produced by the combination of the movement of the hip orthosis and the second winch of the tibial orthosis (which acts on the heel, raising it).
- The upper femur actuator is attached to a belt/harness (ideally for the shoulders), which can be shared with the hip orthosis, and performs a similar movement to lengthen or shorten its strap, simply as compensation for the first movement. Thus the resulting force is not lost in the natural lever of the lower femur actuator on the femur orthosis, or on the thigh, but that the maximum tractive force produces the desired effect (knee extension).

If the patient only needs the femur orthosis, the active elements (winch, strap) of the tibial orthosis can be removed or deactivated, this being used only as a passive orthosis, in order to perform only the knee extension.

Finally, the invention can be constituted as a hip orthosis, formed by a harness that also carries one or more hip actuators. This hip actuator preferably comprises a frontal (solid) pulling system (in front of the user) that modifies the angle so that the direction of effort is initially as parallel to the ground as possible (i.e. allowing the advance with more efficiency). For this, for example, it will have a very high radius so that the movement, at first, is practically straight and horizontal. Later, the leg will be lifted with the rest of the movement of the frontal pulling system.

This hip orthosis can be used independently of the others, or more preferably as a complement to complete user assistance.

All this can have an activation button, so that the system is activated or deactivated when the user needs it and is not at rest or stopped. Moreover, the activation button can be adjusted in response to needs. For example, if the user is going to climb a small step, the hip orthosis may need a somewhat greater performance.

To correct the drop foot, it can comprise a pressure sensor located on the heel floor, which indicates to the CPU when it is raised or in contact with the ground, activating or deactivating the motor (raising or not the toe).

The hip orthosis, among other advantages over the state of the art, solves the mechanical problem of effective energy loss, by not having unwanted movements of the orthosis itself (vertical and lateral). Unlike the previous solutions, which suffered and had to compensate them with synchronized, alternating and opposite movements (pendular movement) to avoid moving the orthosis too much and that the energy dispersed in empty movements of the orthosis. In this way, the hip orthosis can be used to fully replace the locomotor movement of a single limb, without needing a complete exoskeleton, or to repeat the same system on the other leg to compensate. It conforms to natural biomechanics, and does not produce movements outside the natural ambulation, being therefore a substantial innovation, and solving critical mechanical problems, with respect to the mentioned solutions.

DESCRIPTION OF THE DRAWINGS

For a better understanding of the invention, the following figures are included.

EMBODIMENTS OF THE INVENTION

Next, an embodiment of the invention will be briefly described as an illustrative and non-limiting example thereof.

Figure 1:
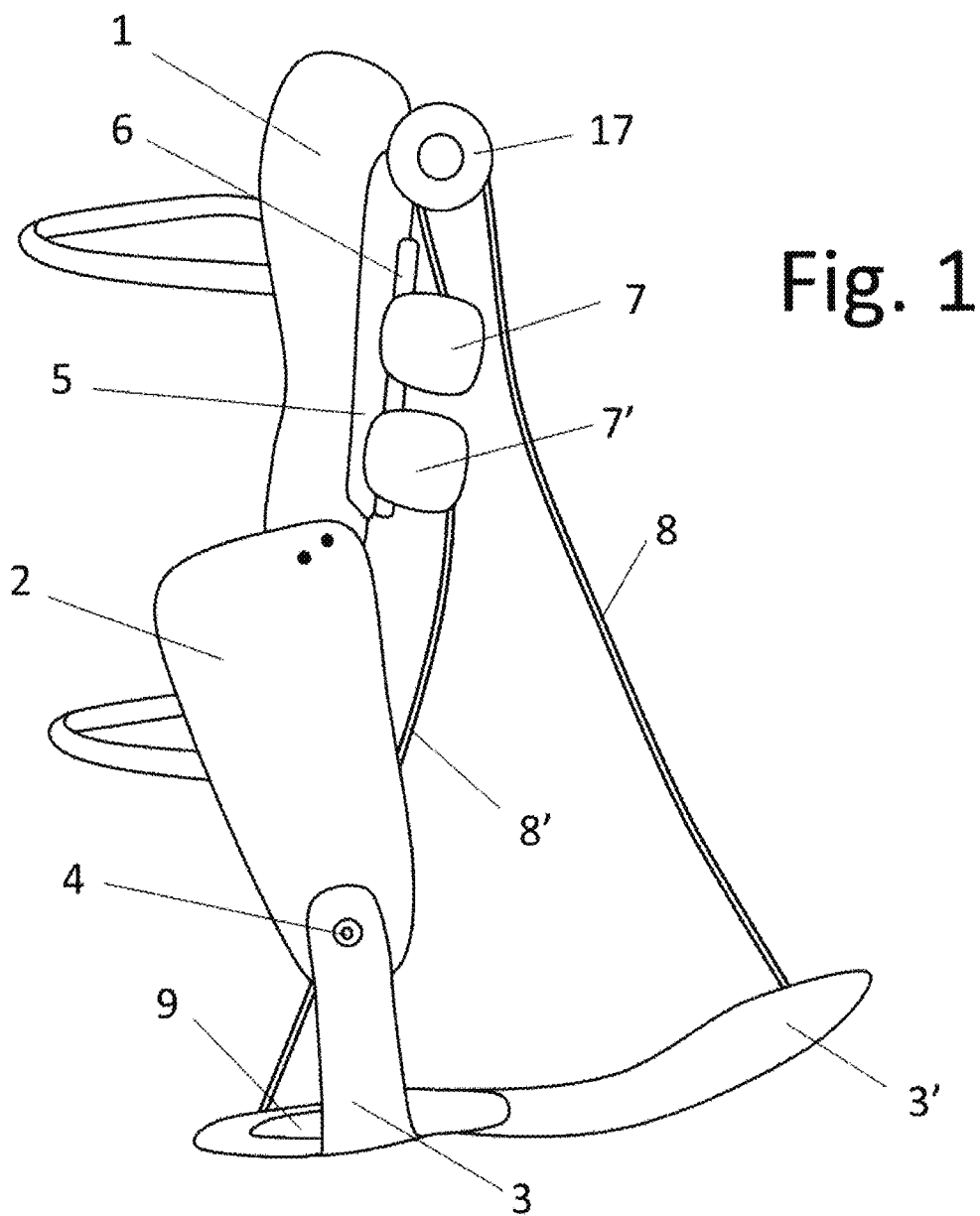
FIG. 1: General view of an example of embodiment of the motorized assistance system, of the tibial orthosis, eliminating wiring to simplify the view.

The tibial orthosis shown in FIG. 1 starts from a tibial support (1), covering the user's shin, which extends to the bottom by means of an ankle fastening (2), and a plantar fastening (3), normally limited to the heel. The attachment between the ankle fastening (2) (one part on each side of the ankle, although only one side is visible) and the plantar fastening (3) is done through a joint (4) that allows the rotation of both. The joint (4) must be aligned with the axis of rotation of the ankle of the user or patient. This alignment will normally be done by a technician.

The tibial fastening (1) has a support (5) for electrical and mechanical equipment, mainly formed by the processor (6) (CPU) and a motorized winch (7) of a strap (8). The free end of the strap (8) is fixed to the foot, near the toe. This fixation can be by means of a loop that surrounds the foot, a hook in the shoe or in an extension (3') of the plantar fastening (3), or another similar system. The position of the winch (7) will preferably be on the longitudinal axis of the foot, so that the strap (8) performs the simplest movement and there are no lateral forces on the winch (7). If desired, bypass pulleys can be installed. The tibia orthosis may have a second winch (7') with its rear strap (8') that performs the opposite movement of the joint. That is, to help raise the heel (in conjunction with the movement of the hip orthosis causes the semi-flexion and unlocking of the knee).

In the simplest solution (drop foot) the processor (6) will start the winch (7) according to the readings of one or more foot position sensors (9) arranged in the plantar fastening (3) or in its extension. The movement of releasing the strap (8) may not be motorized because the foot itself will pull it. Releasing a brake (not shown) will be enough. It is also possible to detect the position of the foot by means of gyroscopes or accelerometers. The foot position sensor (9) has at least one pressure sensor.

The winches (7) and (7') will normally be activated by two servomotors, and the length of the straps (8 and 8') that must be taken up can be regulated, or when the resistance of the foot to the taking up of the straps (8 and 8') exceeds a programmable limit can be detected.

In the simplest solution (drop foot) if desired, although not really necessary, the reaction can be modified if it detects that the user is running or jogging. This modification can be done via software, by detecting an increase in the frequency of pressure changes. In the race, the point of no throw could be lower (higher in the leg travel) or make the upward travel greater.

Figure 2:
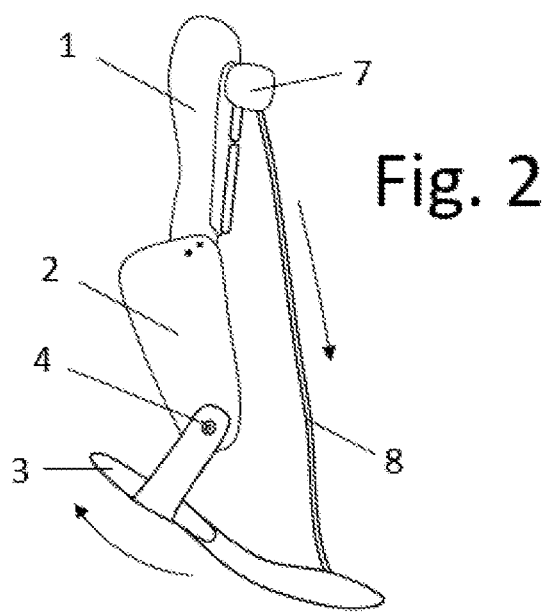
FIG. 2: Diagram of the position of the different elements of another embodiment, at the moment in which the patient lifts the heel from the floor.
Figure 3:
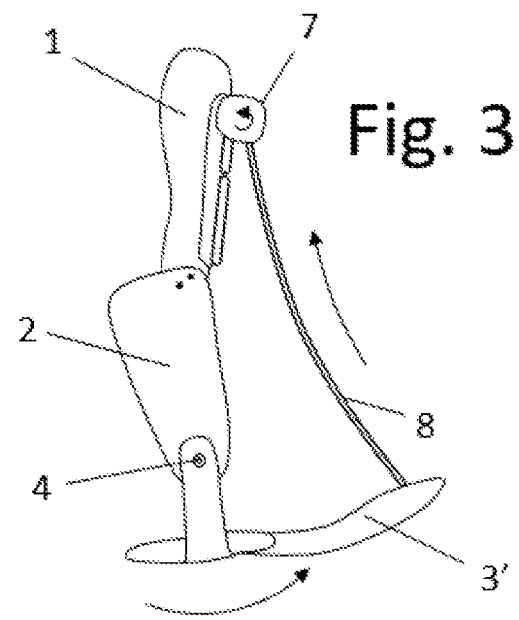
FIG. 3: Scheme of the position of the different elements of the embodiment of FIG. 2, at the moment in which the foot is separated from the ground (in the air).

FIGS. 2 and 3 show the position of the different elements of the tibial orthosis in its simplest solution (drop foot only) during the resting and elevation of the foot. This solution applies to cases where the patient cannot lift the toe.

In the most complex solution (in which the patient cannot lift the heel by himself/herself), said movement would be performed by the second winch (7') in a similar way (winch not represented in these two figures, but in the FIG. 1).

FIG. 2 shows the beginning of the movement in the simplest solution. The patient lifts the heel, causing a pressure sensor (9) to forward the signal so that the CPU/processor (6) commands the winch (7) to start the scheduled taking up of the strap (8) and lift the toe (FIG. 3) by way of strap bypass pulley 17.

In a more complex solution, an external actuator (a button for example) would give the signal to the CPU so that the second winch (7') performed said heel lift. Said movement will occur at the same time as a hip actuator (14) of the hip orthosis that will be indicated below is moved, both complementing to produce the knee release and the effective heel lift (impossible if the knee remains blocked/stretched)

A preprogramed time later, the second winch (7') goes to rest and the winch (7) is activated, as has been already described, at the same time as the winch of the hip orthosis continues with its movement, allowing the effective advance of the leg.

The preferred solution for tibial fastening (1) is to apply a shin guard, which allows the support (5) to be placed in the desired position. On the other hand, the ankle fastening (2) and the plantar fastening (3) can be constituted by an articulated ankle brace. These elements are already available in the market and only would be necessary their union.

Figure 4:
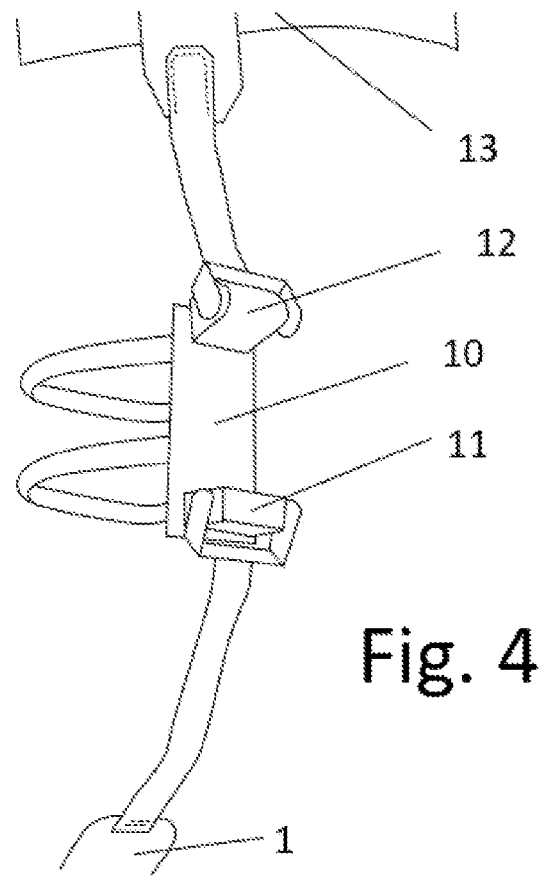
FIG. 4: Schematic view of the upper part of a more advanced embodiment, comprising the femur orthosis.

A more advanced embodiment is shown in FIG. 4, comprising most of the elements of the tibial orthosis, indicated with the same references, as well as a femur orthosis.

The femur orthosis comprises a thigh attachment (10), located above the knee and in front of the patient. The attachment carries two femur actuators (11, 12). The lower femur actuator (11) is attached by a strap to the tibial orthosis. The upper femur actuator (12) is fixed by another strap to a belt, but more preferably to a harness (13) since it must be able to withstand the tension that moves the knee.

When the lower femur actuator (11) is activated, the knee extension occurs. At the same time, the upper femur actuator (12) performs the opposite movement (which also corresponds to lengthening or shortening the corresponding strap) to compensate for efforts and transfer them to the harness (13).

If the patient only needs the femur orthosis, the active elements of the tibial orthosis can be eliminated or deactivated so that all functions are performed by the femur orthosis, passing the tibial orthosis to be a passive orthosis.

Figure 5:
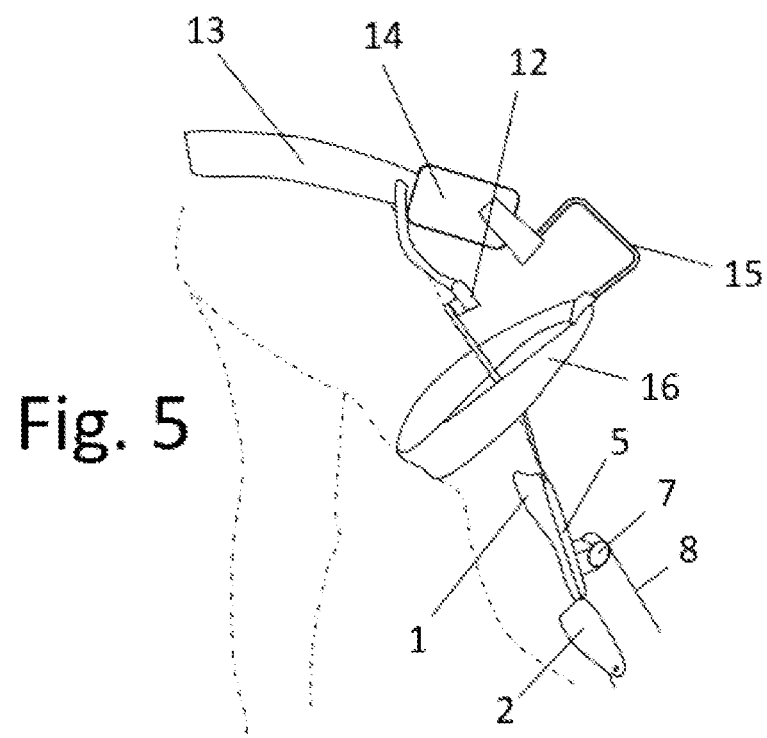
FIG. 5: Schematic view of an even more advanced embodiment, with the three orthoses attached to one leg (in a broken line).

FIG. 5 shows a hip orthosis, which starts from a shoulder harness (13) that is also used for the upper hooking of the femur orthosis. The frontal pulling and operation system is similar to the active parts of the other orthoses. However, the hip actuator (14) that pulls the corresponding strap must be larger, and generally requires a front lever (15) to help redirect the effort. The aim is to ensure that the movement is initially as parallel to the ground as possible rather than upwards (which is the natural movement of any actuator in that position and that of the others described in the invention). The hip actuator (14) will be attached by the lever (15) and its strap to a leg attachment (16), which will normally be a loop or collar and is placed at the front of the thigh. This causes the movement of the hip actuator (14) to generate the swinging of the limb, and finally a slight elevation thereof. The lever (15) changes the turning radius of the hip actuator (14) and the point from which the effort is made on the leg attachment (16).

The supply will preferably be a rechargeable lithium polymer battery with a capacity of 1500 mAh or greater depending on the complexity of the system. The more orthoses must be active, more capacity and power may be necessary.

In use, the most complete version performs the following operations. When the pressure sensor (9), one or more accelerometers, or a button, indicates to the processor (6) that it is time to lift the leg, the hip orthosis unlocks the knee by moving the leg, parallel to the ground, simultaneously, the second winch (7') lifts the heel, causing the knee to half-flex.

In a second phase, the second winch (7'), becomes inactive, and the winch (7) is activated, lifting the toe (at that time the foot is not resting on the ground), while the hip actuator (14) of the hip orthosis (whose movement is continuous), ends the swinging and lifting of the leg, causing it to move forward to the axis of the body.

Finally, in a third phase, the femur orthosis proceeds to extend the knee just before the resting and the system is ready to restart the step with the opposite leg.

The invention claimed is:

1. A motorized assistance system for a tibial orthosis, the motorized assistance system comprising:
   a tibial fastener adapted to cover a shin of a user;
   a plantar fastener;
   a processor adapted to receive an activation signal;
   a power connected to said processor so as to supply power to said processor;
   an ankle fastener adapted to articulate at an axis of an ankle of the user, said ankle fastener being articulated to said plantar fastener, said ankle fastener being joined to said tibial fastener; and
   an active part comprising:
      a femur orthosis having a thigh attachment, said femur orthosis adapted to be positioned above the knee of the user and in front of the user;
      a lower femur actuator attached by a strap to said tibial fastener;
      an upper femur actuator affixed by another strap to a harness or belt, both of said lower femur actuator and said upper femur actuator adapted to act to take up or release the harness or belt in parallel when a foot of the user is not resting on the ground; and
      a hip orthosis formed by another harness or belt that supports a hip actuator, said hip orthosis adapted to be positioned adjacent to a hip of the user, said hip orthosis having a front lever movably connected thereto, the front lever adapted to a frontal portion of a thigh of the user.

2. The motorized assistance system of claim 1, further comprising:
   a foot position sensor arranged in said plantar fastener, said foot position sensor having at least one pressure sensor.

3. The motorized assistance system of claim 2, wherein said foot position sensor comprises at least one accelerometer.

4. The motorized assistance system of claim 2, wherein said foot position sensor comprises at least one gyroscope.

5. The motorized assistance system of claim 1, wherein said processor is carried on said femur orthosis.

6. The motorized assistance system of claim 1, wherein the strap of said lower femur actuator has a free end taken up by a winch, the strap of lower femur actuator having a loop, the loop adapted to surround the foot of the user.

7. The motorized assistance system of claim 1, wherein the strap of said lower femur actuator has a free end taken up by a winch, the strap of lower femur actuator having a hook adapted to connect to a shoe of the user.

8. The motorized assistance system of claim 1, wherein the strap of said lower femur actuator has a free end taken up by a winch, the strap of lower femur actuator having a hook connected to an extension of said plantar fastener.

9. The motorized assistance system of claim 6, wherein the winch is adapted to release an adjustable amount of the strap.

10. The motorized assistance system of claim 6, wherein the winch is adapted to stop when a resistance of the strap exceeds a predetermined limit.

11. The motorized assistance system of claim 1, wherein the tibial fastener comprises a shin guard.

12. The motorized assistance system of claim 1, wherein said ankle fastener and said plantar fastener comprise an articulated ankle brace.

13. The motorized assistance system of claim 1, further comprising:
   a motorized winch having a support with a strap having a free end adapted to be fixed on a foot of the user, said motorized winch and the strap being carried by said tibial fastener, said motorized winch adapted to take up the strap thereof when the foot of the user is not resting on the ground.

14. The motorized assistance system of claim 2, wherein said processor receives the activation signal from the foot position sensor when the foot position sensor detects that the foot position sensor is not resting on the ground.

15. The motorized assistance system of claim 6, wherein said tibial orthosis has another winch adapted to be attached to a heel of the foot of the user by a back strap.

* * * * *